United States Patent [19]

Kabeta

[11] Patent Number: 4,921,976

[45] Date of Patent: May 1, 1990

[54] VINYL-CONTAINING UNSATURATED ORGANOSILICON COMPOUND AND PROCESS FOR PREPARING THE SAME

[75] Inventor: Keiji Kabeta, Gunma, Japan

[73] Assignee: Toshiba Silicone Co., Ltd., Tokyo, Japan

[21] Appl. No.: 272,032

[22] Filed: Nov. 16, 1988

[30] Foreign Application Priority Data

Nov. 18, 1987 [JP] Japan ................ 62-291541

[51] Int. Cl.⁵ ............................ C07F 9/08; C07F 7/18
[52] U.S. Cl. .................................. 556/482; 556/445;
556/484; 556/485; 556/465
[58] Field of Search ............... 556/445, 482, 484, 485,
556/465

[56] References Cited

U.S. PATENT DOCUMENTS

| | | | |
|---|---|---|---|
| 4,297,499 | 10/1981 | Koga et al. | 556/465 |
| 4,408,017 | 10/1983 | Martin | 556/465 X |
| 4,623,741 | 11/1986 | Watanabe et al. | 556/465 |
| 4,642,356 | 2/1987 | Langver et al. | 556/465 X |

Primary Examiner—Paul F. Shaver

Attorney, Agent, or Firm—Sughrue, Mion, Zinn, Macpeak & Seas

[57] ABSTRACT

A silicon compound represented by formula (I):

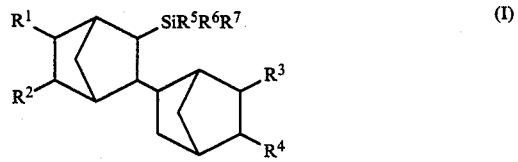

wherein either one of $R^1$ and $R^2$ represents a vinyl group with the other representing a hydrogen atom; either one of $R^3$ and $R^4$ represents a vinyl group with the other representing a hydrogen atom; and $R^5$, $R^6$, and $R^7$, which may be the same or different, each represents a substituted or unsubstituted monovalent hydrocarbon group, an alkoxy group or a halogen atom. The compound exhibits improved compatibility with polymerizable monomers or organic polymers and is useful as a crosslinking agent or modifier.

7 Claims, 3 Drawing Sheets

VINYL-CONTAINING UNSATURATED ORGANOSILICON COMPOUND AND PROCESS FOR PREPARING THE SAME

FIELD OF THE INVENTION

This invention relates to an unsaturated organosilicon compound having two vinyl groups per molecule which is useful as a crosslinking agent or modifier for organic polymers and to a process for preparing the same.

BACKGROUND OF THE INVENTION

Known organosilicon compounds having a vinyl group include vinyltrichlorosilane, vinyltriethoxysilane, vinylmethyldiethoxysilane, vinyltris(methoxyethoxy)silane, and so on. These organosilanes are well known as silane coupling agents effective for improving physical properties of composite materials comprising organic polymers and inorganic fillers, and improving characteristics or adhesiveness of a surface of solid materials or inorganic fillers. They are also widely used as crosslinking agents or modifiers for various organic polymers.

It is known in the art that a vinyl group bonded to a silicon atom behaves differently from that bonded to a carbon atom so that introduction of a vinylsilane into organic polymers has been limited in various processes and still the art has encountered difficulty. Moreover, use of a vinylsilane has been limited due to its poor compatibility with organic compounds or organic polymers.

In an attempt to overcome these disadvantages, there have been proposed silicon compounds containing an alkenyl-substituted phenyl group (e.g., p-vinylphenyl group) as disclosed in JP-A-62-215608 (the term "JP-A" as used herein means an "unexamined published Japanese patent application") and silicon compounds containing a 5-vinylbicyclo[2.2.1]heptyl group. However, these silicon compounds, though effective as modifiers for organic polymers, are not always satisfactory as a crosslinking agent or crosslinking aid.

SUMMARY OF THE INVENTION

One object of this invention is to provide an organosilicon compound having a highly reactive alkenyl group and an organic group as large as possible bonded to the silicon atom, which is useful as a co-crosslinking agent for copolymerizable monomers or organic polymers owing to its high reactivity and increased compatibility with the polymerizable monomers or organic polymers.

Another object of this invention is to provide a process for preparing the above-described compound with industrial advantages.

As a result of extensive investigations, the inventor has found that the above objects of this invention can be accomplished by a vinylbicycloheptyl group-containing silicon compound in a dimer form represented by formula (I):

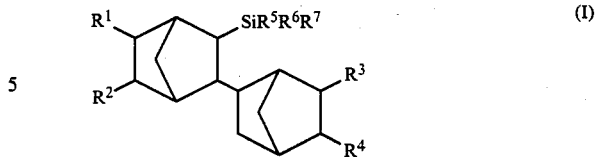

wherein either one of $R^1$ and $R^2$ represents a vinyl group with the other representing a hydrogen atom; either one of $R^3$ and $R^4$ represents a vinyl group with the other representing a hydrogen atom; and $R^5$, $R^6$, and $R^7$, which may be the same or different, each represents a substituted or unsubstituted monovalent hydrocarbon group, an alkoxy group or a halogen atom.

The compound of formula (I) can be prepared by reacting 5-vinylbicyclo[2.2.1]hept-2-ene represented by formula (II):

and a silane compound represented by formula (III):

wherein $R^5$, $R^6$, and $R^7$ are as defined above, in the presence of, as a catalyst, metallic palladium or a palladium complex containing no phosphorus compound as a ligand. The product of the reaction can easily be isolated from the reaction mixture at high yield and high purity by distillation under reduced pressure.

BRIEF DESCRIPTION OF THE ACCOMPANYING DRAWINGS

DETAILED DESCRIPTION OF THE INVENTION

Figure 1:
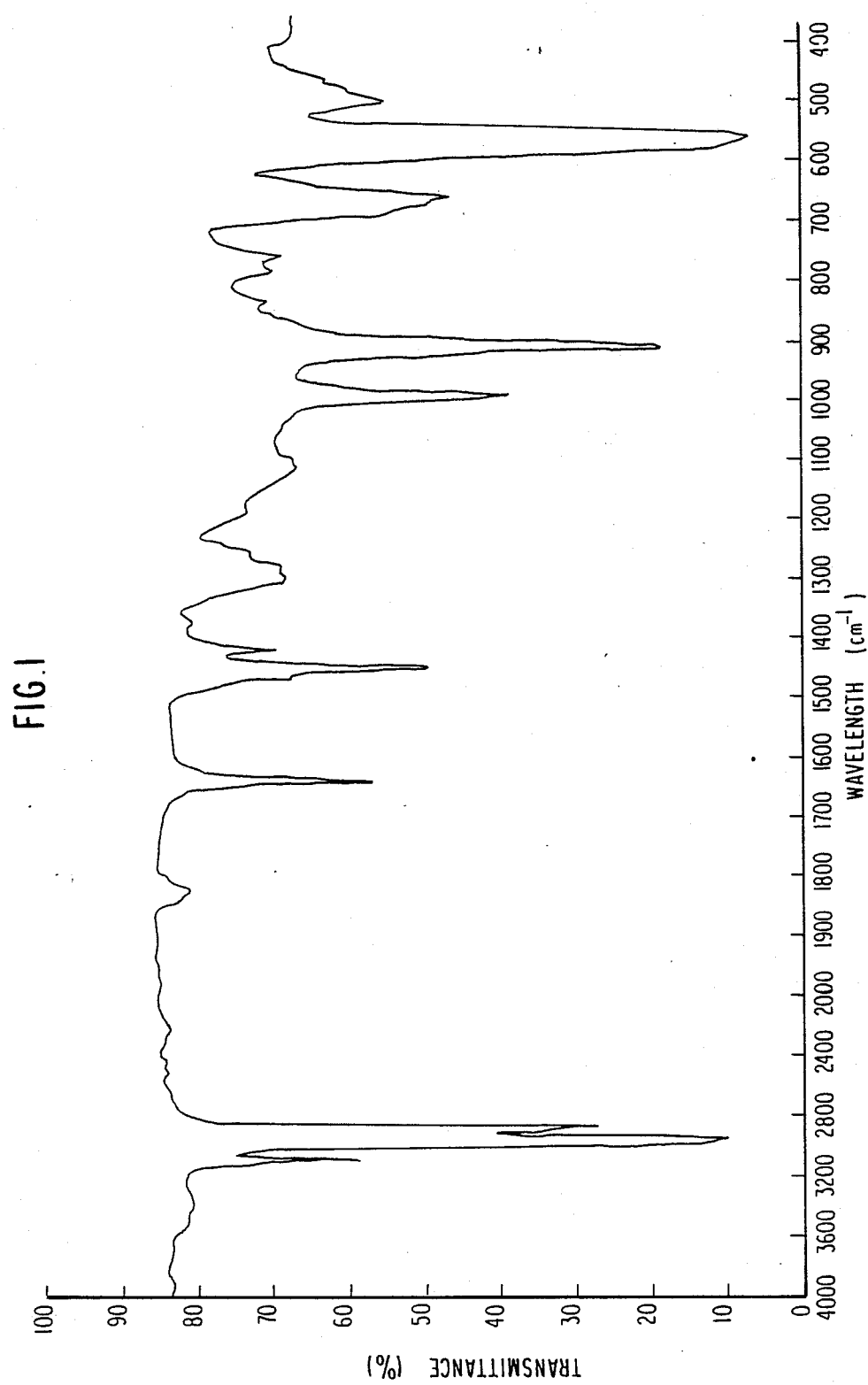
FIGS. 1 and 2 are IR and NMR spectra, respectively, of the compound prepared in Example 1.

The starting compound of formula (II), 5-vinylbicyclo[2.2.1]hept-2-ene, has a carbon-carbon double bond in each of the endocyclic moiety and the exocyclic moiety. Upon reacting, because of the difference in reactivity between these two double bonds, the double bond in the endocyclic moiety is preferentially subjected to the reaction to accomplish dimerization and silylation simultaneously while the vinyl group of the exocyclic moiety remains untouched.

In Formula (III), the substituted or unsubstituted monovalent hydrocarbon group as represented by $R^5$, $R^6$ or $R^7$ includes an alkyl group (e.g., methyl, ethyl, propyl, butyl and hexyl groups), a cycloalkyl group (e.g., cyclopentyl and cyclohexyl groups), an aralkyl group (e.g., 2-phenylethyl group), an aryl group (e.g., phenyl and tolyl groups), and a substituted hydrocarbon group (e.g., chloromethyl, chlorophenyl and 3,3,3-trifluoropropyl groups). The alkoxy group as represented by $R^5$, $R^6$ or $R^7$ includes methoxy, ethoxy, propoxy and butoxy groups. The halogen atom as represented by $R^5$, $R^6$ or $R^7$ includes fluorine, chlorine, bromine and iodine atoms, with chlorine being preferred in view of its hydrolyzability and availability.

Specific examples of the silane compound of formula (III) are trimethylsilane, triethylsilane, dimethylethylsilane, dimethylpropylsilane, dimethylphenylsilane, trimethoxysilane, triethoxysilane, tripropoxysilane, and trichlorosilane. Preferred of them is trichlorosilane from the standpoint of reaction yield.

The palladium catalyst which can be used in this invention may be any of metallic palladium, 0-valent or 2-valent complexes of palladium. It should be noted, however, that the palladium complexes should not contain a phosphorus compound as a ligand. If a palladium complex having a phosphorus compound as a ligand is used as a catalyst, the reaction produces a by-product represented by formula (IV):

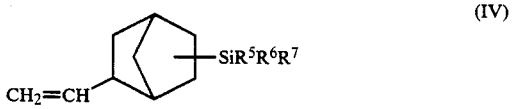
(IV)

wherein $R^5$, $R^6$, and $R^7$ are as defined above, in high yield, whereas the desired compound of formula (I) is not substantially obtained or obtained only in a very low yield.

Specific examples of the catalysts usable in the present invention are metallic palladium (e.g., palladium-on-charcoal) and divalent complexes, e.g., dichlorobis(benzonitrile)palladium (II), dibromobis(benzonitrile)palladium (II), dichlorobis(acetonitrile)palladium (II), dichloro(1,5-cyclooctadiene)palladium (II), dichlorobis($\eta$-allyl)palladium (II), bis(acetylacetonato)palladium (II), palladium dichloride, etc. From the viewpoint of reactivity and yield, preferred of them are palladium charcoal, dichlorobis(benzonitrile)palladium (II), dichloro(1,5-cyclooctadiene)palladium (II), and bis(acetylacetonato)palladium (II).

As a relevant technique, it has been reported to use chloroplatinic acid as a catalyst in the reaction between bicyclo[2.2.1]hepta-2-ene (a compound of formula (II) wherein the vinyl group is displaced with a hydrogen atom) and trichlorosilane as described in *J. Gen. Chem. USSR*, Vol 31, No. 4, 1109–1117 (1961). In this case, however, the product corresponding to the compound of formula (I) is obtained only in a low yield, proving this catalyst inapplicable to the present invention.

The amount of the palladium catalyst to be used preferably ranges from 0.001 to 5.0 parts by weight, more preferably from 0.1 to 1.0 part by weight, per 100 parts by weight of 5-vinylbicyclo[2.2.1]hept-2-ene. If it is less than 0.001 part by weight, the reaction rate is insufficient. Amounts exceeding 5.0 parts by weight bring about no further improvement of reaction rate, only resulting in bad economy.

The amount of the silane compound of formula (III) to be charged is not particularly critical but preferably ranges from 0.4 to 1.0 mol per mol of 5-vinylbicyclo[2.2.1]hept-2-ene. The hydrosilylation reaction can be carried out at a temperature between −30° C. and 150° C., preferably between 10° C. and 110° C. The reaction is usually effected under atmospheric pressure or, if desired, under pressure or reduced pressure.

In carrying out the present invention, while any of the silane compounds of formula (III) is employable, it is a matter of course that trichlorosilane is selected in view of reaction yield and then the resulting product can be alkoxylated or alkylated by the Grignard reaction.

A reaction solvent is not essentially required, but a solvent inert to the silane compound may be used for the purpose of increasing the solubility of the catalyst or effecting temperature control. Included in such a solvent are hydrocarbon solvents, e.g., toluene, xylene, cylohexane, n-hexane, n-heptane, naphtha, mineral spirit, petroleum benzene, etc.; halogenated hydrocarbon solvents, e.g., chloroform, carbon tetrachloride, trichloroethylene, perchloroethylene, 1,1,1-trichloroethylene, etc.; ether solvents, e.g., ethyl ether, tetrahydrofuran, ethylene glycol diethyl ether, etc.; ester solvents, e.g., ethyl acetate, butyl acetate, amyl acetate, etc.; ketone solvents, e.g., acetone, methyl ethyl ketone, methyl isobutyl ketone, etc.; and aprotic polar solvents, e.g., dimethylformamide, dimethylacetamide, etc.

The reaction time is not particularly specified as it varies depending on the kinds of the starting material, catalyst and solvent or the reaction temperature. In general, reaction conditions are set so as to complete the reaction within a period of from 0.5 to 6 hours.

The reaction can be effected in a usual manner. For example, a mixture of 5-vinylbicyclo[2.2.1]hept-2-ene and a palladium catalyst is heated to a prescribed temperature while stirring, and the silane compound such as trichlorosilane is added thereto dropwise. Since the reaction proceeds at high selectivity, the resulting product can be purified easily by distillation. It is possible to ensure heat stability of the product by adding an appropriate antioxidant to the reaction mixture prior to distillation or adding an appropriate amount of such an antioxidant to the purified compound.

According to the process of the present invention, the vinylbicycloheptyl-containing silane compound having a dimer form can be produced at high yield and high purity on an industrial scale. Since the thus produced silane compound has large-sized organic groups containing a highly reactive vinyl group in the exocyclic moiety, it exhibits satisfactory compatibility with other polymerizable monomers or organic polymers. In addition, the compound carries a silicon atom to which a hydrolyzable group or a stable organic group is bonded.

Accordingly, the compound of the present invention not only functions as a monomer easily providing copolymers with double bond-containing organic monomers but also serves as a grafting agent, crosslinking agent or modifier for other organic polymers or as a coupling agent or adhesion-promoting agent for a solid surface.

The present invention is now illustrated in greater detail with reference to the following Examples and Comparative Examples, but it should be understood that the present invention is not deemed to be limited thereto. In these examples, all the parts and percents are by weight unless otherwise indicated.

EXAMPLE 1

In a four-necked flask equipped with a reflux condenser having a calcium chloride tube, a thermometer, and a stirrer were charged 240 parts (2.0 mol) of 5-vinylbicyclo[2.2.1]hept-2-ene and 0.25 part of 10% palladium-on-charcoal, and the mixture was heated to 80° C. while stirring. To the mixture was added dropwise 175 parts (1.29 mol) of trichlorosilane over a period of 3 hours, followed by heating at 90° C. for 2 hours while stirring. After completion of the reaction, the reaction mixture was distilled under reduced pressure (2 mmHg) to obtain 233 parts (yield: 62%) of fraction having a boiling point of 173° to 175° C. as a colorless transparent liquid.

The resulting fraction was analyzed by determining the refractive index, specific gravity, IR spectrum, NMR spectrum and mass spectrum, and by elementary analysis. The results obtained are shown in Table 1 below. From these results, the product was identified to be a compound of the following formula:

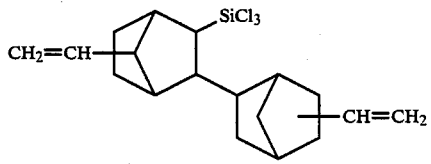

Figure 2:
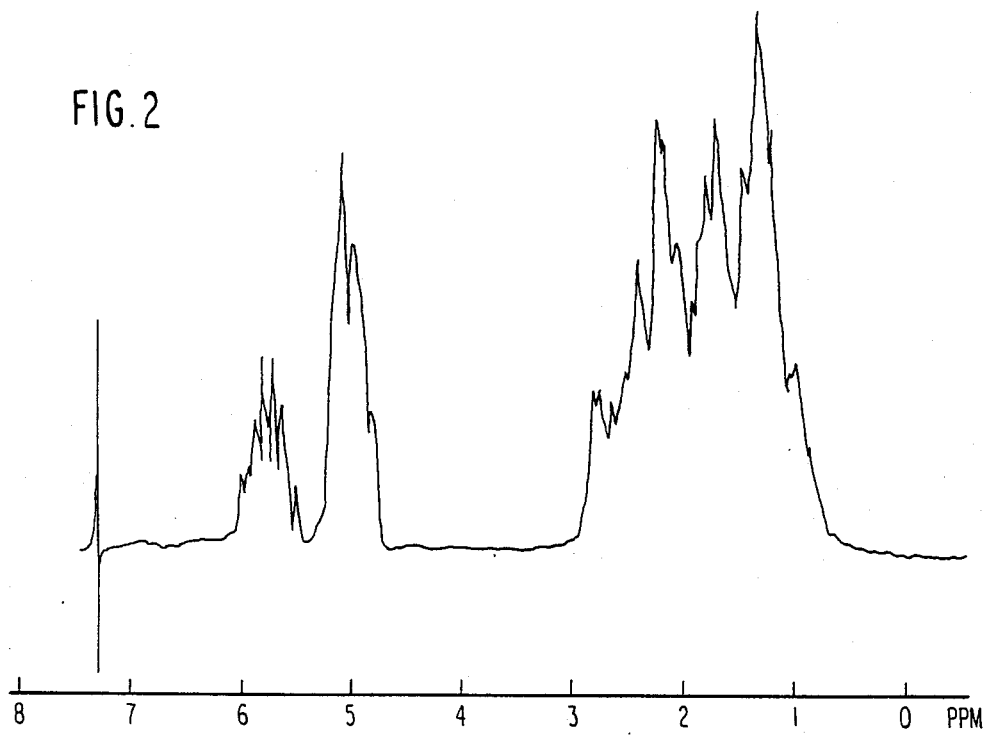

The purity of the product was found to be 99.2% by gas chromatography. The IR and NMR spectra of the compound are shown in FIGS. 1 and 2, respectively.

The initial boiling fraction was similarly analyzed and, as a result, was found to be 5-vinylbicyclo[2.2.1-]heptyltrichlorosilane and its isomer.

EXAMPLE 2

In the same four-necked flask as used in Example 1 were charged 132 parts of n-hexane, 38.4 parts (1.2 mol) of methanol, and 63.2 parts (0.8 mol) of pyridine, and 75.1 parts (0.2 mol) of the reaction product as obtained in Example 1 was added dropwise to the mixture under stirring while maintaining the mixture at 20° C. or less. After the dropwise addition, the stirring was further continued at room temperature for an additional two hours. The reaction mixture was filtered to remove by-produced pyridine hydrochloride, and the filtrate was distilled under reduced pressure to obtain 63.2 parts (87%) of a colorless transparent liquid fraction having a boiling point of 130° to 131° C./1.0 mmHg. The product was analyzed in the same manner as in Example 1, and the results obtained are shown in Table 1. It was confirmed that the product is a compound of Example 1 with chlorine atoms thereof displaced with a methoxy group. The compound was found to have a purity of 99.9% by gas chromatography.

EXAMPLE 3

Figure 4:
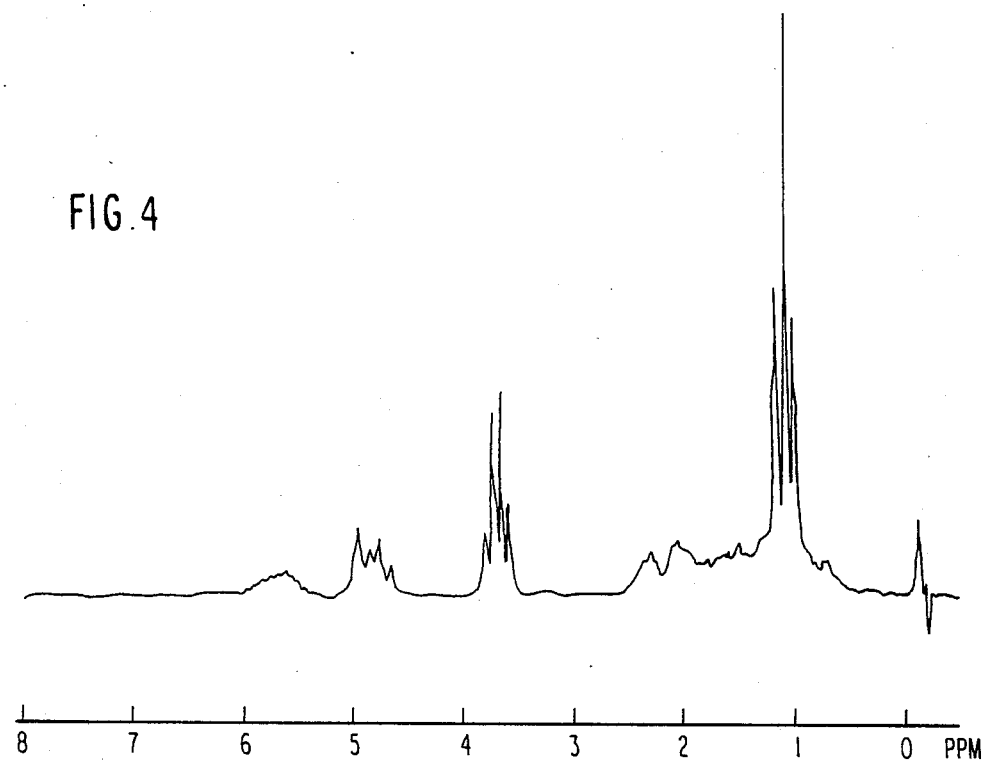
FIGS. 3 and 4 are IR and NMR spectra, respectively, of the compound prepared in Example 3.
Figure 3:
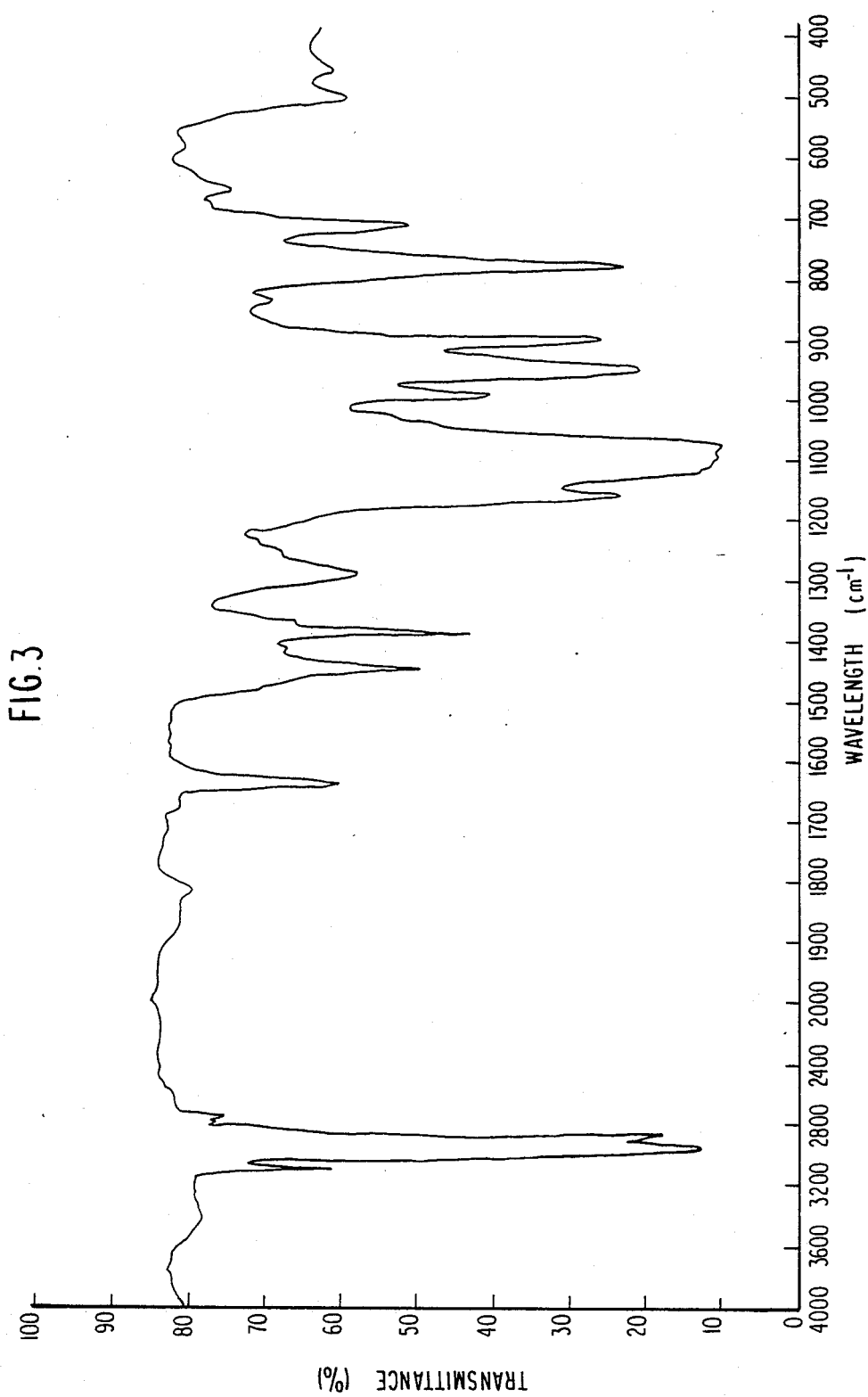

In the same manner as in Example 2, except for replacing methanol with 55.2 parts (1.2 mol) of ethanol, 72.0 parts (89%) of an ethoxy-substituted derivative having a boiling point of 160° to 161° C./1.5 mmHg as a colorless transparent liquid was obtained. The results of analyses are shown in Table 1. The purity of the compound was found to be 99.8% by gas chromatography. The IR and NMR spectra of the compound are shown in FIGS. 3 and 4, respectively.

EXAMPLE 4

In the same four-necked flask as used in Example 1 were charged 20.2 parts (0.05 mol) of the triethoxysilane derivative as prepared in Example 3 and 100 ml of diethyl ether, and 50 ml of a diethyl ether solution of methyl magnesium bromide (titre=1.0) was added dropwise to the mixture over 1 hour under stirring while maintaining the mixture at 20° C. After the dropwise addition, the stirring was further continued for an additional one hour. The by-produced magnesium chloride was separated by filtration. The filtrate, after removing diethyl ether therefrom, was subjected to distillation under reduced pressure to obtain 11.4 parts (61%) of a fraction having a boiling point of 155° to 156° C./2.0 mmHg as a colorless transparent liquid. As a result of the same analyses as in Example 1, the product was identified to be a compound having the following formula:

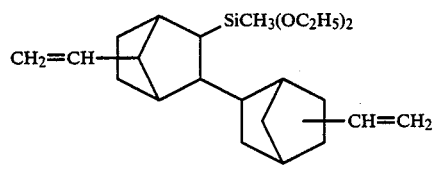

As a result of gas chromatography, the compound was found to have a purity of 99.4%.

EXAMPLE 5

In the same manner as in Example 1, except for replacing the palladium-on-charcoal by 0.1 part of dichlorobis(benzonitrile)palladium, 228 parts (61%) of a product was obtained. The analytical results and purity of the product were entirely the same as those of Example 1.

COMPARATIVE EXAMPLE 1

In the same manner as in Example 5, except for replacing the palladium catalyst as used in Example 5 with 0.1 part of dichlorobis(triphenylphosphine)palladium, 297 parts of a colorless transparent liquid having a boiling point of 85° to 87° C./4 mmHg was obtained. The results of analyses on the product were as follows.

Refractive Index: $n_D^{25}$ 1.5080
Specific Gravity: $d_4^{25}$ 1.229
IR Spectrum (liquid film method): 3070 cm$^{-1}$ ($\nu$CH of double bond), 2950 and 2860 cm$^{-1}$ (aliphatic $\nu$CH), 1635 cm$^{-1}$ ($\nu$C=C), 990 and 910 cm$^{-1}$ ($\delta$CH of double bond)
NMR Spectrum (90 MHz; solvent: CCl$_4$; internal standard: TMS): 0.95–3.00 ppm (m, 10H, aliphatic proton), 5.00–5.10 ppm (m, 2H, proton of vinyl group) 5.95–6.10 ppm (m, 1H, proton of vinyl group)

From these analytical results, the resulting fraction was identified to be 5-vinylbicyclo[2.2.1]heptyltrichlorosilane and its position isomer. The yield was 90%, and the purity was 98.5% as determined by gas chromatography.

COMPARATIVE EXAMPLE 2

The procedure of Comparative Example 1 was repeated, except for using 0.5 part of 5% platinum-on-charcoal as a catalyst. The resulting reaction product was distilled under reduced pressure to obtain a transparent liquid having a boiling point of 85° to 89° C./4 mmHg. As a result of the same analyses as in Comparative Example 1, the fraction was confirmed to be a mixture of 5-vinylbicyclo[2.2.1]heptyltrichlorosilane and 5-(2-trichlorosilylethyl)bicyclo[2.2.1]hept-2-ene and to contain no desired compound.

A high-boiling content of the residue after the distillation was found to be 9.8% by gas chromatography.

TABLE 1

| | Example 1 | Example 2 | Example 3 | Example 4 |
|---|---|---|---|---|
| $R^5$; $R^6$; $R^7$ | Cl; Cl; Cl | OMe; OMe; OMe | OEt; OEt; OEt | Me; OEt; OEt |
| Boiling Point (°C./mmHg) | 173–175/2.0 | 130–131/1.0 | 160–161/1.5 | 155–156/2.0 |
| Refractive index ($n_D^{25}$) | 1.5340 | 1.4989 | 1.4877 | 1.4880 |
| Specific Gravity ($d_4^{25}$) | 1.191 | 1.045 | 1.005 | 1.003 |
| IR Spectrum (cm$^{-1}$) | 3070 ($\nu$CH of double bond) 2950 (aliphatic $\nu$CH) 2860 (aliphatic $\nu$CH) 1640 ($\nu$C=C) 990 ($\delta$C=C) 910 ($\delta$C=C) | 3070 ($\nu$CH of double bond) 2950 (aliphatic $\nu$CH) 2860 (aliphatic $\nu$CH) 2840 (aliphatic $\nu$CH) 1640 ($\nu$C=C) 1090 ($\delta$Si—O—C) 990 ($\delta$C=C) 910 ($\delta$C=C) | 3070 ($\nu$CH of double bond) 2950 (aliphatic $\nu$CH) 2860 (aliphatic $\nu$CH) 1640 ($\nu$C=C) 1100 ($\delta$Si—O—C) 990 ($\delta$C=C) 910 ($\delta$C=C) | 3070 ($\nu$CH of double bond) 2950 (aliphatic $\nu$CH) 2860 (aliphatic $\nu$CH) 1640 ($\nu$C=C) 1280 ($\nu$Si—Me) 1100 ($\delta$Si—O—C) 990 ($\delta$C=C) 910 ($\delta$=C) |
| NMR Spectrum (ppm) | 0.70–2.95 (m, 19H, aliphatic CH), 4.72–5.35 (m, 4H, double bond CH), 5.35–6.15 (m, 2H, double bond CH), | 0.60–2.80 (m, 19H, aliphatic CH), 3.57 (s, 9H, —OCH$_3$), 4.70–5.20 (m, 4H, double bond CH), 5.50–6.17 (m, 2H, double bond CH) | 0.60–2.80 (m, 19H, aliphatic CH), 1.20 (t, J = 7Hz, 9H, OCCH$_3$), 3.80 (q, J = 7Hz, 6H, OCH$_2$), 4.70–5.20 (m, 4H, double bond CH), 5.50–6.17 (m, 2H, double bond CH) | 0.04 (s, 3H, Si—CH$_3$), 0.60–2.80 (m, 19H, aliphatic CH), 1.20 (t, J = 7Hz, 6H, OCCH$_3$), 3.80 (q, J =7Hz, 4H, OCH$_2$), 4.70–5.20 (m, 4H, double bond CH), 5.50–6.17 (m, 2H, double bond CH) |
| Mass Spectrum (M+) | 374 | 362 | 404 | 374 |
| Elementary Analysis (%)* | C: 57.46 (57.48) H: 6.70 (6.70) Si: 7.46 (7.47) Cl: 28.38 (28.35) | C: 69.53 (69.56) H: 9.48 (9.45) Si: 7.74 (7.75) | C: 71.23 (71.24) H: 9.97 (9.96) Si: 6.94 (6.94) | C: 73.71 (73.74) H: 10.19 (10.22) Si: 7.48 (7.50) |

Note: *Values in the parentheses are calculated values.

While the invention has been described in detail and with reference to specific embodiments thereof, it will be apparent to one skilled in the art that various changes and modifications can be made therein without departing from the spirit and scope thereof.

What is claimed is:

1. A silicon compound represented by formula (I):

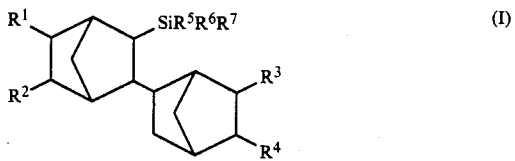

wherein either one of $R^1$ and $R^2$ represents a vinyl group with the other representing a hydrogen atom; either one of $R^3$ and $R^4$ represents a vinyl group with the other representing a hydrogen atom; and $R^5$, $R^6$, and $R^7$, which may be the same or different, each represents a substituted or unsubstituted monovalent hydrocarbon group, an alkoxy group or a halogen atom.

2. A compound of claim 1, wherein $R^5$, $R^6$, and $R^7$ each represents a halogen atom.

3. A compound of claim 1, wherein $R^5$, $R^6$, and $R^7$ each represents a chlorine atom.

4. A compound of claim 1, wherein $R^5$, $R^6$, and $R^7$ each represents an alkoxy group.

5. A compound of claim 1, wherein $R^5$, $R^6$, and $R^7$ each represents a methoxy group.

6. A compound of claim 1, wherein $R^5$, $R^6$, and $R^7$ each represents an ethoxy group.

7. A process for preparing a silicon compound represented by by formula (I):

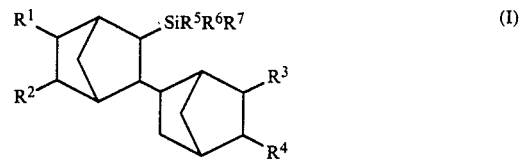

wherein either one of $R^1$ and $R^2$ represents a vinyl group with the other representing a hydrogen atom; either one of $R^3$ and $R^4$ represents a vinyl group with the other representing a hydrogen atom; and $R^5$, $R^6$, and $R^7$, which may be the same or different, each represents a substituted or unsubstituted monovalent hydrocarbon group, an alkoxy group or a halogen atom, comprising reacting 5-vinylbicyclo[2.2.1]hept-2-ene represented by formula (II):

and a silane compound represented by formula (III):

wherein $R^5$, $R^6$, and $R^7$ are as defined above, in the presence of, as a catalyst, metallic palladium or a palladium complex containing no phosphorus compound as a ligand and purifying the product by distilling the reaction mixture.

* * * * *